United States Patent [19]
Hoberg

[11] Patent Number: 5,766,352
[45] Date of Patent: Jun. 16, 1998

[54] STRIPE APPLICATOR DEVICE

[75] Inventor: Ted C. Hoberg, Mission Viejo, Calif.

[73] Assignee: Kuntz Mfg. Co., Inc., Santa Ana, Calif.

[21] Appl. No.: 584,131

[22] Filed: Jan. 11, 1996

[51] Int. Cl.$^6$ .............. B05B 7/06; G01N 21/00; B65M 75/14
[52] U.S. Cl. .............. 118/313; 118/315; 118/58; 422/65; 242/610; 242/908
[58] Field of Search ................ 118/300, 313, 118/315, 257, 263, 207–208, 235, 305, 307, 58; 422/100, 102, 104, 65; 242/908, 610

[56] References Cited

U.S. PATENT DOCUMENTS

| | | | |
|---|---|---|---|
| 3,012,863 | 12/1961 | Feichtmeir | 422/100 |
| 3,828,723 | 8/1974 | Herman | 118/325 |
| 3,901,656 | 8/1975 | Durkos et al. | 422/64 |
| 4,204,012 | 5/1980 | Brocklehurst et al. | 118/669 |
| 4,576,113 | 3/1986 | Kambara et al. | 118/697 |
| 4,857,133 | 8/1989 | Mullen | 156/387 |
| 4,865,872 | 9/1989 | Pellatiro | 118/313 |

Primary Examiner—Donald E. Czaja
Assistant Examiner—Calvin Padgett
Attorney, Agent, or Firm—Lyon & Lyon LLP

[57] ABSTRACT

A stripe applicator device that facilitates the accurate and efficient striping of a membrane with a reagent solution while avoiding cross-contamination between adjacent reagent stripes, preferably has a pay-out assembly, an applicator assembly having a plurality of nozzles aligned along a line that forms an obtuse angle with the line of travel of a membrane material from the pay-out assembly, a drying chamber and an take-up assembly having a pinch-roller assembly driven by a motor to draw the membrane material from the pay-out assembly through the applicator assembly and drying chamber.

21 Claims, 4 Drawing Sheets

STRIPE APPLICATOR DEVICE

SPECIFICATION

1. Field of the Invention

This invention relates to striping devices and, more particularly, to a stripe applicator that facilitates accurate and efficient introduction of reagent fluids onto a membrane.

2. Background of the Invention

Reagent chemicals are used for the purpose of detecting, measuring, examining, or analyzing other substances. In certain methods of diagnostic testing, it is preferable that a large number of reagent types be used to test for various properties of a particular substance or solution simultaneously. The testing tool used to accomplish this is typically a relatively small strip of a membrane material upon which different reagents are applied. Typically, the membrane strip is about ⅛ inches wide by three inches long. The reagents are applied in a manner to form reagent test stripes along the membrane strip. For accurate testing, high purity and high sensitivity, without cross-contamination, are essential requirements of the reagents. Accordingly, the density, width and location of the reagent stripes on the membrane material are critical to achieving the necessary purity and sensitivity for accurate testing.

Membrane test strips are typically made by first applying a series of reagent stripes along an elongated piece of membrane material and then cutting the elongated piece of membrane into relatively small strips. The devices currently used to apply the reagent stripes to the elongated piece of membrane material tend to lack the requisite accuracy as the number of reagent stripes is increased.

To form the reagent stripes on the elongated membrane, these devices typically use either a modified air nozzle to spray a reagent fluid onto the membrane, or a syringe tip nozzle to drop small overlapping droplets of the reagent fluid onto the membrane. Although these nozzles are effective, the risk of cross-contamination from splatter or errant sprays increases as the distance between adjacent reagent stripes decreases, and as the pressure driving the reagents increases.

In addition, the current stripe applicator devices have shortcomings with regard to material waste. These devices usually mount the membrane to a platform which is then traversed by a group of nozzles to apply the reagent stripes to the membrane. To properly align the stripes on the elongated membrane, the membrane must be mounted on the platform of the striping device and, then, tested to determine if the stripes are properly aligned on the membrane. This procedure is time consuming and generally wastes about 40% of the membrane material. The membrane material is commonly made of nitrocellulose filtration media. Since nitrocellulose filtration media is relatively expensive, excessive waste of this material is undesirable.

Therefore, it is desirable to have a stripe applicator device that is able to accurately and efficiently apply reagent stripes to a membrane, that maintains high reagent purity and sensitivity while avoiding cross-contamination between adjacent reagent stripes, and that produces a minimal amount of waste membrane material.

SUMMARY OF THE INVENTION

The stripe applicator device of the present invention serves to facilitate the accurate and efficient application of reagent stripes to a membrane, the maintenance of high reagent purity and sensitivity and the avoidance of cross-contamination between adjacent reagent stripes, and serves to minimize membrane material waste.

The stripe applicator device of the present invention preferably has a rigid frame with a table top mounted thereon, a pay-out assembly mounted on the forward end of the frame, a take-up assembly mounted on the aft end of the frame, an applicator assembly mounted on the frame between the pay-out assembly and the accumulator assembly, and a drying chamber mounted on the frame between the applicator assembly and the take-up assembly. A spool of membrane material is mounted on the pay-out assembly which includes a pay-out reel and an accumulator pulley assembly. The membrane material from the spool of membrane material is drawn from the pay-out assembly through the applicator assembly, across the vacuum plate, and through the drying chamber by a pinch-roller assembly, and then through an accumulator pulley assembly by a take-up reel in the take-up assembly.

The applicator assembly preferably includes a base mounted on the frame, a nozzle plate connected to a slide which is slidably received over linear slide shafts extending from the base, a plurality of nozzle assemblies mounted on the nozzle plate, a vacuum plate mounted on the base between the nozzle plate and the base, and a plurality of vials comprising reagent solutions that are interconnected to the nozzle assemblies. A vacuum is drawn through the vacuum plate to maintain the membrane material in a flat surface for accurate striping.

The nozzle assemblies include a nozzle, having a capillary orifice, mounted in the nozzle plate, a tensioning block mounted to a tensioning base which is mounted on the nozzle plate, a spring mounted between the tensioning block and tensioning base and attached to the nozzle, and a tension adjustment screw mounted in the tensioning block and exerting a downward force on the spring. Each of the nozzles of the nozzle assemblies are aligned along a line that forms an obtuse angle with the longitudinal axis of the nozzle plate. The longitudinal axis of the nozzle plate is parallel to the line of travel of the membrane material.

A pressure chamber encompasses the plurality of pressure vials to force the reagent solution from the vials through a flexible supply tube to the nozzles. The pressure in the pressure chamber is preferably maintained at a level to supplement the capillary action of the orifice of the nozzle.

Alternatively, the vials are mounted in a vial holder which is adjustably attached to the base. The vial holder can be raised to an elevation which provides sufficient head pressure to supplement the capillary action of the orifice of the nozzle after the nozzle has been primed.

An object of the present invention is to provide an improved stripe applicator device.

Further objects and advantages of the present invention will become apparent from a consideration of the drawings and ensuing description.

DESCRIPTION OF THE PREFERRED EMBODIMENT

Figure 1:
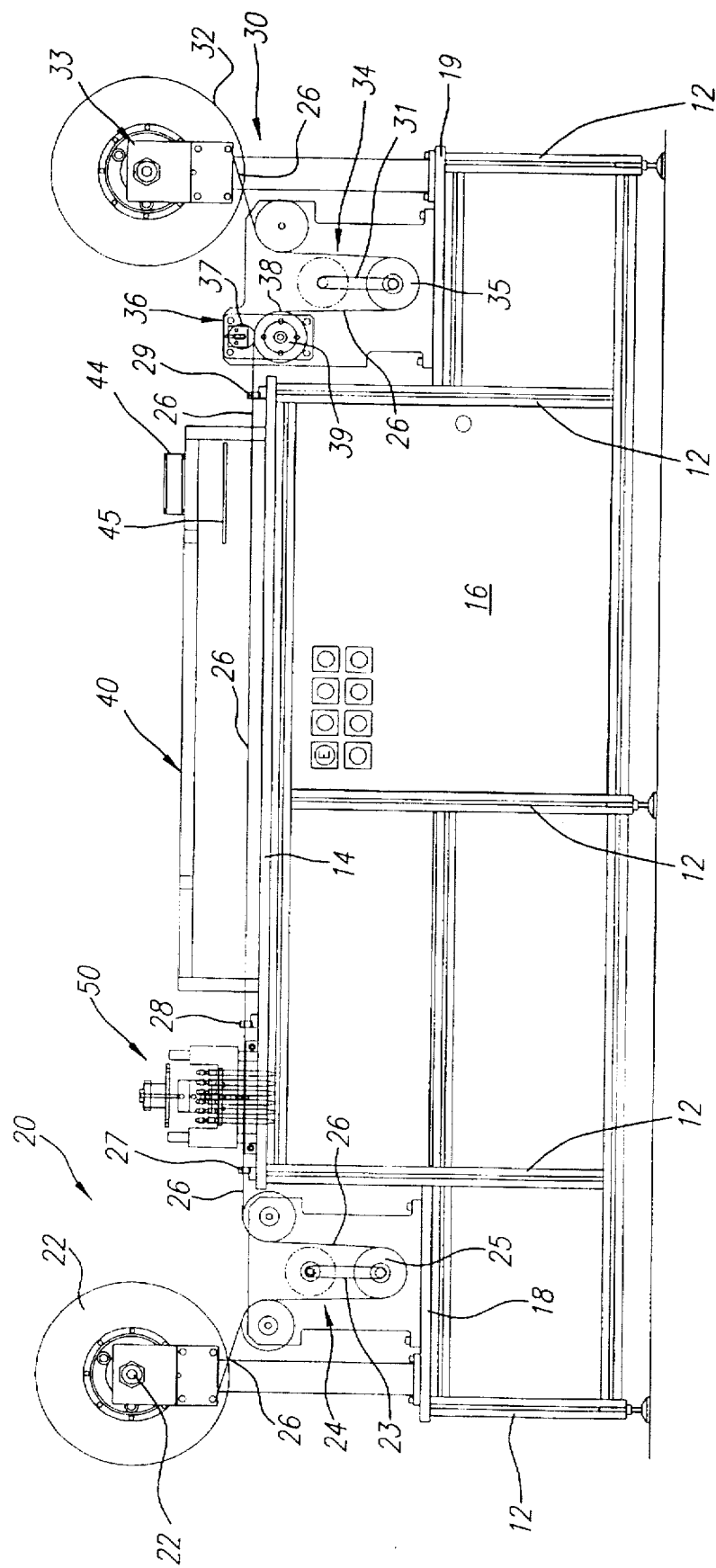
FIG. 1 is a front view of the stripe applicator device of the present invention.

Referring now in detail to the drawings, therein illustrated is a novel stripe applicator device 10. As shown in FIG. 1, the stripe applicator device 10 preferably comprises a table top 14 mounted on top of a preferably rigid steel frame 12. An electrical enclosure 16 housing all of the machine controls (not shown) is mounted within the frame 12. The machine controls preferably include a programmable logic controller (PLC). A pay-out table 18 and a take-up table 19 are mounted on the frame 12 forward and aft of the table top 14, respectively, and at a lower elevation than the table top 14.

A pay-out assembly 20, which is mounted on the pay-out table 18, comprises a pay-out reel 22 preferably driven by a variable speed motor 21 and a accumulator pulley assembly 24. A spool of membrane material 26 is mounted on the pay-out reel 22. As the spool of membrane material 26 unwinds, the membrane material passes through the accumulator pulley assembly 24 and then passes over the table top 14 while being guided by membrane guides 27, 28 and 29 mount ed to the table top 14. The accumulator pulley assembly 24 includes an idler pulley 25 mounted on a spring loaded slide 23. A sensor (not shown) is positioned within the accumulator pulley assembly 24 to sense the vertical location of the idler pulley 25 along the slide 23. The sensor is interconnected to the PLC which intermittently activates and deactivates the variable speed motor 21 depending on the location of the idler pulley 25 on the slide 23. The PLC activates the variable speed motor 21 to dispense the membrane material 26 from the pay-out reel 22 into the accumulator pulley assembly 24. This operation will be discussed in greater detail below.

Mounted on top of the table top 14 is an applicator assembly 50, which will be discussed in detail below, and a drying chamber 40. The membrane material 26 passes through the applicator assembly 50 where the reagents, which are immersed in fluid, are applied to the membrane material 26 by striping the membrane material 26. The membrane material 26 then passes through the drying chamber 40 where a fan 44 provides counter flow air circulation over the membrane material 26 to dry the newly applied reagent stripes S. The air flow of the fan 44 is adjustable to provide thorough drying of the stripes S. Preferably, the fan 44 is capable of providing up to 1000 cubic feet of air per minute.

In addition to the fan 44, a heater 45 may be used in the drying chamber 40 to provide additional drying capabilities for the drying chamber 40. The heater is preferably capable of heating the air in the drying chamber up to 50 degrees Centigrade above the ambient air temperature. Depending upon the reagents and the membrane material used by the operator, and depending on how fast the operator wishes to take-up the membrane material 26, the fan 44 and the heater 45 may be used in conjunction, separately or not at all to provide thorough drying of the reagent stripes S.

A take-up assembly 30, which is mounted on the take-up table 19, comprises a take-up reel 32, an accumulator pulley assembly 34 and a pinch-roller assembly 36. The membrane 26 enters the take-up assembly 30 after exiting the drying chamber 40. The membrane 26 passes through the pinch-roller assembly 36 and the accumulator pulley assembly 34 and, then, is attached to the take-up reel 32 where it is wound into a spool.

The pinch-roller assembly 36 includes a pincher 37 which is operably connected to a roller 38. The pincher 37 exerts a force against the roller 38 to prevent the membrane 26 from traveling in a reverse direction and thereby maintaining tension in the membrane 26 to keep it flat and straight. In addition, the configuration of the pinch-roller 36 enables the roller 38, which is driven by a motor 39, to pull the membrane 26 through the stripe applicator device 10 into the accumulator pulley assembly 34. Preferably, the motor 39 that drives the roller 38, is a variable speed stepper type motor with a power rating of less than one-half horsepower. The operator can adjust the speed of the motor 29 and, hence, the speed of the roller 38, to ensure that the reagent stripes S are being applied at a proper thickness and density, and are dried thoroughly.

The take-up reel 32 also preferably includes a variable speed motor 33 to rotate the take-up reel 32 at speed required to effectively wind-up the membrane material 26. The accumulator pulley assembly 34 also includes an idler pulley 35 mounted on a spring loaded slide 31 and a sensor (not shown) which is interconnected to the PLC. The PLC intermittently activates the motor 33 to take-up the membrane material 26 on the take-up reel 32 as it accumulates in the accumulator pulley assembly 34. The PLC activates and deactivates the motor 33 depending on the vertical location of the idler pulley 35 sensed by the sensor. This operation will be discussed in more detail below.

Figure 2:
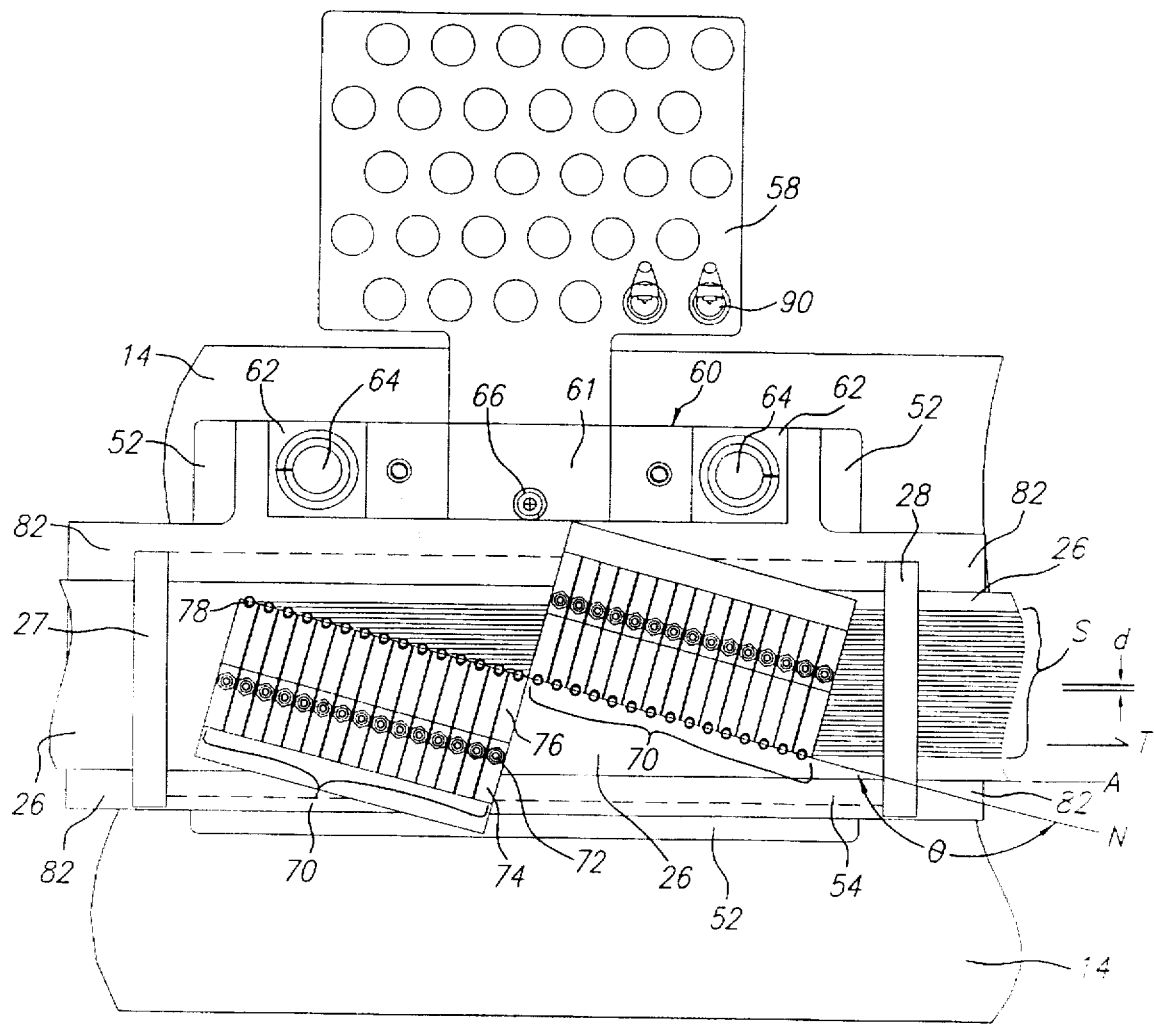
FIG. 2 is a top view of the applicator assembly of the stripe applicator device of the present invention.
Figure 3:
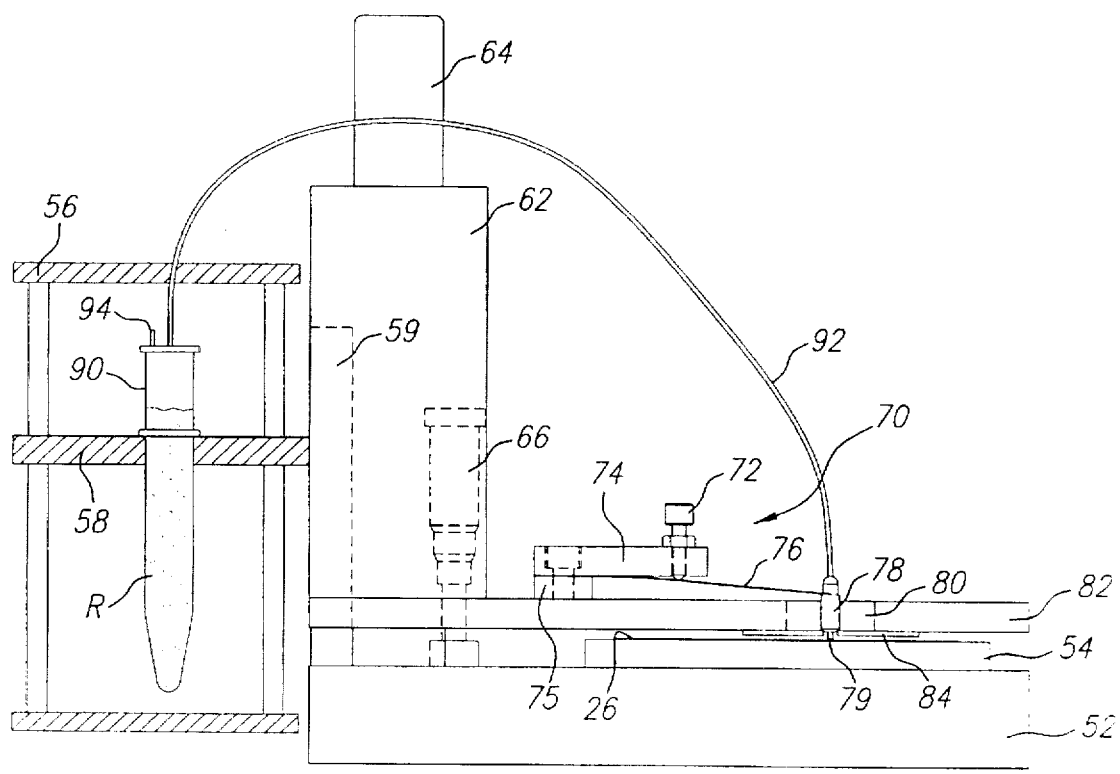
FIG. 3 is a partial side view of the applicator assembly of the stripe applicator device of the present invention.

Turning to FIGS. 2 and 3, the applicator assembly 50 is shown in detail. The applicator assembly 50 comprises a base 52 mounted on the table top 12. A vacuum plate 54, which is mounted on top of the base 52 applies a vacuum to the bottom side of the membrane material 26 to maintain the membrane material in a flat orientation as it passes over the vacuum plate 54 and, thus, provide a flat surface to be striped. Preferably, the source of the vacuum is adjustable and capable of drawing up to one bar of vacuum. The vacuum source may alternatively be a vacuum pump or venturi vacuum generator mounted on the stripe applicator device, or may be provided by the facility in which the stripe applicator device 10 is installed.

Projecting perpendicularly and upwardly from the base 52 is a pair of linear slide shafts 64. A linear slide 60, having a pair of slide collars 62 extending from a slide base 61, is slidably received over the linear slide shafts 64. A micrometer 66 is mounted through the slide base 61 of the linear slide 60. The micrometer 66 maintains the linear slide 60 in spaced relation with the base 52.

A nozzle plate 82, which is attached to the slide base 61 of the linear slide 60, extends perpendicularly outward from the slide 60 and parallel to the base 52 and the vacuum plate 54. As shown in FIG. 2, the nozzle plate 82 has a longitudinal axis A that is parallel to the direction of travel T of the membrane material 26. Preferably thirty nozzle assemblies 70, each having a nozzle 78, are mounted on the nozzle plate 82. The nozzles 78 are advantageously configured to line up along a line N which forms an obtuse angle e with the longitudinal axis A of the nozzle plate 82. This configuration is preferred because as the angle e is increased, the center line distance d between adjacent nozzles 72, and thus, adjacent reagent stripes S, is decreased. As a result, a greater number of reagent stripes S can be applied to the membrane material without increasing the risk of cross-contamination.

Referring to FIG. 3, a single nozzle assembly 70 comprises a tensioning block 74 attached at one end to a tensioning base 75 to form a cantilever configuration. The tensioning base 75 is mounted on the nozzle plate 82 and maintains the tensioning block 74 spaced from and parallel to the nozzle plate 82. A spring 76 is mounted, at one end, between the tensioning block 74 and the tensioning base 75, also forming a cantilever configuration. The end of the spring 76 that is opposite the tensioning base 75, extends beyond the end of the tensioning block 74 and connects to a nozzle 78. The nozzle 78 is mounted in a bushing 80 fixedly mounted in the nozzle plate 82. A nozzle retainer 84 is fixed to the bottom of the nozzle plate 82 to retain the nozzle 78 in place within the bushing 80. A tension adjustment screw 72 is rotatably mounted in the end of the tensioning block 74 opposite the tensioning base 75. The tension adjustment screw 72 abuts the spring 76 and exerts a downward force on the spring 76.

The nozzle 78 has a capillary orifice 79 which is preferably capable of forming a 0.8 millimeter wide stripe. The nozzle 78 is connected via a flexible supply tube 92 to a vial 90. The vial 90 has a pressure vent 94 and is filled with a chemical reagent R immersed in a solution. Preferably, the vial 90 is sized to hold enough reagent solution R to stripe a minimum of one thousand feet of membrane material 26. Each individual nozzle 78 is connected to a separate vial 90 via a flexible supply tube 92.

The individual vials 90 are all retained in a vial holder 58 which is mounted to a stanchion 59 extending upwardly from the base 52. A pressure chamber 56 encompasses the vials 90 and the vial holder 58. The pressure chamber 56 is pressurized with an inert gas alternatively supplied from nitrogen or dry air bottles, or from a supply in the facility in which the stripe applicator device 10 is installed. The pressurized gas enters the vial 90 through the pressure vent 94 to force the reagent solution R from the vial 90 through the supply tube 92 to the nozzle 78 and out through the orifice 79. The pressure of the gas preferably is adjustable up to two psi, so as to provide pressure sufficient to supplement the capillary action of the capillary orifice 79 and provide a continuous even flow of reagent solution R onto the membrane 26.

Figure 4:
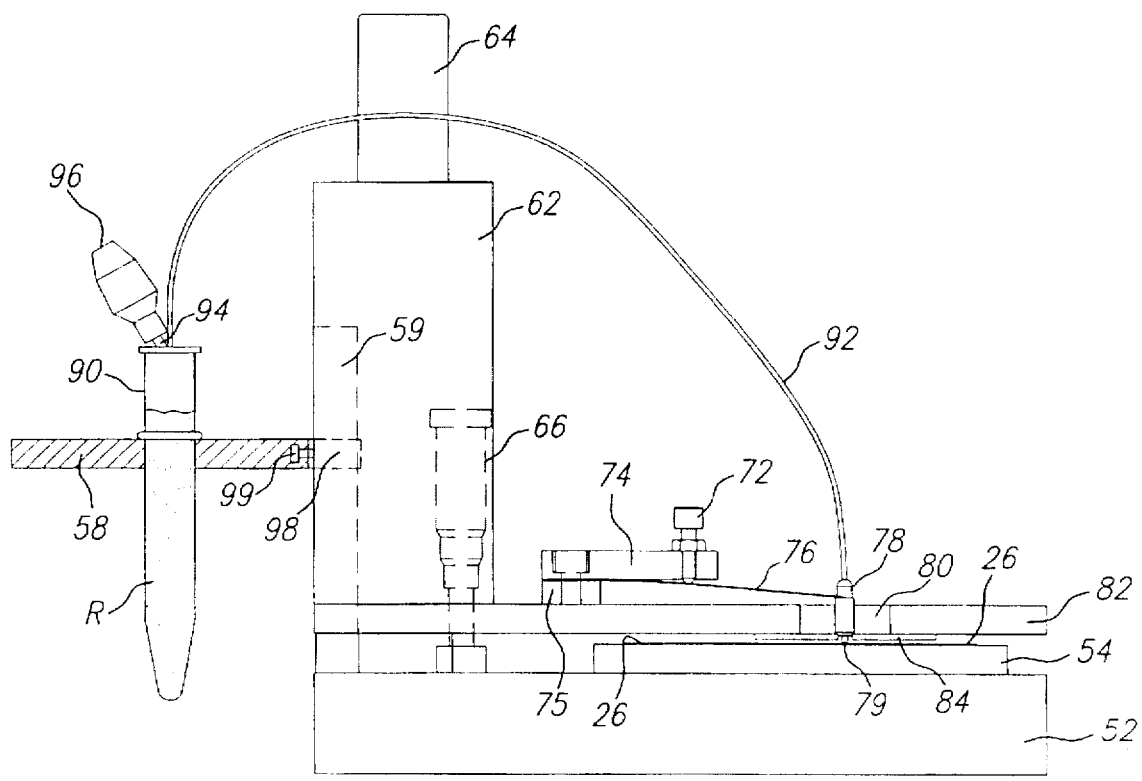
FIG. 4 is a partial side view of an alternate embodiment of the applicator assembly of the stripe applicator device of the present invention.

In an alternative embodiment, shown in FIG. 4, the pressure chamber 56 is removed. A primer pump 96 is attached to the pressure vent 94 of the vial 90 and the vial holder 58 includes a vial holder slide 98 which slidably connects the vial holder 58 to the stanchion 59. A head adjustment screw 99 is used to fix the vial holder slide 98 in place along the stanchion 59. The vial holder 58 can be elevated to a height that provides sufficient head pressure to continue to supplement the capillary action of the orifice 79 of the nozzle 78 after the nozzle 78 has been primed by the primer pump 96.

In operation, a spool of membrane material 26 is mounted on the pay-out reel 22. The configuration of the stripe applicator device 10 (see FIG. 1) enables the user to use a spool of membrane material 26 having an elongated leader (not shown) made of ordinary paper attached to the free end of the member material 26. This leader advantageously allows the user to set-up and test the stripe applicator device 10 without wasting substantially any membrane material 26.

After the spool of membrane material 26, with the paper leader, is mounted on the pay-out reel 22, the paper leader is fed through the accumulator pulley assembly 24, the first guide 27, the applicator assembly 50, the second guide 28, the drying chamber 40, the third guide 29, the pinch-roller assembly 36, and the accumulator pulley assembly 34, and then attached to the take-up reel 32. While being fed through the applicator assembly 50, the nozzles 78 can be conveniently moved upwardly away from the paper leader by raising the slide 60 up the linear slide shaft 64 which moves the nozzle plate 82 upwardly away from the vacuum plate 54 and the base 52.

Prior to running the stepper motor 39 on the roller 38 of the pinch-roller assembly 36, the nozzle plate 82 and slide 60 are lowered to their operating position. The stepper motor 39 is then turned on and the leader begins to be drawn through the applicator assembly 50 and the drying chamber 40. The micrometer 66 can be used to make a common adjustment to all the nozzles 78 by adjusting the height of the nozzle plate 82 relative to the vacuum plate 54. However, the individual reagent stripes can be further fine tuned, i.e., the thickness or density of the stripes can be fine tuned, by adjusting the tension adjustment screw 72. Adjustment of the tension adjustment screw 72 acts to increase or decrease the downward force the spring 76 exerts on the nozzle 78. Because the nozzle 78 is able to retract upward against the force of the spring 76, the use of the spring 76 ensures that the nozzles 78 are less likely to be damaged if the adjustment screw 72 has been adjusted too much and the spring 76 forces the nozzle 78 too far down.

After fine tuning each nozzle 78, the nozzle plate 82 is raised away from the vacuum plate 54 and base 52 until the paper leader has completely passed the applicator assembly 50. If the micrometer 66 is not adjusted, the fine tune adjustment of the nozzles 78 will be maintained. Once the membrane 26 is in place below the nozzles 78 on the vacuum plate 54, the nozzle plate 82 is lowered back into operating position and the striping of the membrane material 26 commences with very little waste of the membrane material 26.

After the membrane material 26 travels through the applicator assembly 50 and is striped with reagent solutions R from the various vials 90, the membrane material 26 passes through the drying chamber 40 where the reagent stripes are dried. Preferably, the membrane material 26 is being wound up by the take-up reel 32 at a rate that allows sufficient exposure to the drying chamber 40 so the reagent stripes can be thoroughly dried.

As noted above, the membrane material 26 is advantageously held flat by the vacuum plate 54 to ensure that the striping is being done on a flat and even surface. The pinch-roller assembly 36 and the accumulator pulley assemblies 24 and 34 also assist in maintaining the membrane material 26 in a flat and even surface. As the roller 38 draws the membrane material 26 through the stripe applicator device 10, the idler pulley 25 begins to travel upwardly against the spring force in the slide 23 until the sensor senses that the idler pulley 25 has reached a predetermined maximum vertical position on the slide 23. This information is transmitted to the PLC which in turn activates the motor 21 on the pay-out reel 22 to dispense the membrane material 26 into the accumulator pulley assembly 24. The motor 21 on the pay-out reel 22 will run until the sensor senses that the idler pulley 25 has reached a predetermined minimum vertical position on the slide 23 and the PLC deactivates the motor 21.

Similarly, the motor 33 on the take-up reel 32 is activated by the PLC when the sensor senses that the idler pulley 35 has reached a predetermined minimum vertical position on the slide 31 and is deactivated by the PLC when the sensor senses that the idler pulley 35 has reached a predetermined maximum vertical position on the slide 31. Thus, the membrane material 26 is maintained relatively straight, flat and even as it travels through the stripe applicator device.

While the above description contains many specificities, these should not be construed as limitations on the scope of the invention, but rather as an exemplification of a preferred embodiment thereof. Other variations are possible.

Accordingly, the scope of the present invention should be determined not by the embodiments illustrated above, but by the appended claims and their legal equivalents.

What is claimed is:

1. A stripe applicator comprising a base, a nozzle plate operably connected to said base, and a plurality of nozzle assemblies mounted on said nozzle plate and adapted to dispense a plurality of stripes in spaced relation along the length of a piece of material, each of said nozzle assemblies comprising a nozzle mounted in said nozzle plate, said nozzle having a capillary orifice, a tensioning base mounted on said nozzle plate, a tensioning block having first and second ends, said first end of said tensioning block being attached to said tensioning base, a spring having first and second ends, said first end of said spring being mounted interposed between said tensioning base and said first end of said tensioning block, said second end of said spring extending beyond said second end of said tension block and attaching to said nozzle, and a tension adjustment screw rotatably mounted in said second end of said tensioning block and operably connected to said spring to adjust the spacing between said nozzle and said base and thereby adjust the thickness and density of a stripe dispensed from said nozzle.

2. The stripe applicator of claim 1, wherein said nozzle of each of said plurality of nozzles being aligned along a line forming an obtuse angle with a longitudinal axis of said nozzle plate to reduce the center line distance between adjacent stripes of a plurality of stripes dispensed from said plurality of nozzle assemblies.

3. A stripe applicator comprising a base, a nozzle plate operably connected to said base, said nozzle plate having a longitudinal axis, a vacuum plate mounted on said base interposed between said nozzle plate and said base, said vacuum plate being adapted to apply a vacuum to a length of material to maintain the length of material in a generally flat orientation, and a plurality of nozzles mounted in said nozzle plate, said plurality of nozzles being adapted to dispense a plurality of stripes in spaced relation along a length of material, each nozzle of said plurality of nozzles being aligned along a line forming an obtuse angle with said longitudinal axis of said nozzle plate to decrease the center line distance between adjacent stripes of a plurality of stripes dispensed by said plurality of nozzles.

4. A stripe applicator comprising a base, a nozzle plate operably connected to said base, said nozzle plate having a longitudinal axis, a linear slide shaft extending from said base, a slide slidably received over said slide shaft and connected to said nozzle plate, said slide and said nozzle plate being adjustably mounted in spaced relation to said base, and a plurality of nozzles mounted in said nozzle plate, said plurality of nozzles being adapted to dispense a plurality of stripes in spaced relation along a length of material, each nozzle of said plurality of nozzles being aligned along a line forming an obtuse angle with said longitudinal axis of said nozzle plate to decrease the center line distance between adjacent stripes of a plurality of stripes dispensed by said plurality of nozzles.

5. The stripe applicator of claim 4, further comprising a micrometer mounted on said slide to maintain and adjust the spacing between said nozzle plate and said base.

6. A stripe applicator comprising a base, a nozzle plate operably connected to said base, said nozzle plate having a longitudinal axis, a plurality of nozzles mounted in said nozzle plate, said plurality of nozzles being adapted to dispense a plurality of stripes in spaced relation along a length of material, each nozzle of said plurality of nozzles being aligned along a line forming an obtuse angle with said longitudinal axis of said nozzle plate to decrease the center line distance between adjacent stripes of a plurality of stripes dispensed by said plurality of nozzles, a plurality of tensioning bases mounted on said nozzle plate, a plurality of tensioning blocks having first and second ends, each one of said tensioning blocks being attached at its first end to a separate one of said plurality of tensioning bases and extending parallel to said nozzle plate, a plurality of springs having first and second ends, said first ends of said plurality of springs being mounted interposed between said plurality of tensioning bases and said first ends of said plurality of tensioning blocks, each of said second ends of said plurality of springs extending beyond said second ends of said plurality of tensioning blocks and attaching to a separate one of said plurality of nozzles, and a plurality of tension adjustment screws rotatably mounted in said second ends of said plurality of tensioning blocks, and each one of said plurality of tension adjustment screws being operably connected to a separate one of said plurality of springs.

7. A stripe applicator comprising a base, a nozzle plate operably connected to said base, said nozzle plate having a longitudinal axis, a plurality of nozzles mounted in said nozzle plate, said plurality of nozzles being adapted to dispense a plurality of stripes in spaced relation along a length of material, each nozzle of said plurality of nozzles being aligned along a line forming an obtuse angle with said longitudinal axis of said nozzle plate to decrease the center line distance between adjacent stripes of a plurality of stripes dispensed by said plurality of nozzles, each of said plurality of nozzles comprise a capillary orifice, and a plurality of vials, each one of said plurality of vials storing a fluid having a chemical reagent emersed therein, and a plurality of supply tubes, each one of said supply tubes interconnecting one of said plurality of vials with one of said plurality of nozzles.

8. The stripe applicator of claim 7, further comprising a pressure vent formed in each one of said plurality of vials, and a pressure chamber connected to said base, said plurality of vials being retained within said pressure chamber, said pressure chamber being adapted to exert pressure on the fluid within said plurality of vials through said pressure vents.

9. The stripe applicator of claim 7, further comprising a vial holder adjustably connected to said base, said plurality of vials being retained in said vial holder to adjust the head pressure that supplements the capillary action of said capillary orifices of said plurality of nozzles.

10. The stripe applicator of claim 9, further comprising a plurality of primer pumps, each one of said plurality of primer pumps being connected to a separate one of said plurality of vials.

11. A stripe applicator device comprising a frame having a first and second ends, a pay-out assembly mounted on said frame adjacent said first end of said frame, said pay-out assembly having a spool of membrane material mounted thereon, a take-up assembly mounted on said frame adjacent said second end of said frame, and an applicator assembly mounted on said frame interposed between said pay-out assembly and said take-up assembly, said applicator assembly being adapted to dispense a plurality of stripes in spaced relation along the length of the membrane material from said spool of membrane material, said applicator assembly including a plurality of nozzles having capillary orifices, said plurality of nozzles being positioned along a first line forming an obtuse angle with a second line parallel to the direction of travel of the membrane material to reduce the spacing between adjacent stripes of a plurality of stripes dispensed by said plurality of nozzles, a base mounted on said frame, a nozzle plate operably connected to said base, said plurality of nozzles being mounted in said nozzle plate, and a vacuum plate adapted to supply a vacuum to the membrane material to maintain the membrane material in a generally flat orientation as it passes through said applicator assembly, said vacuum plate being mounted on said base interposed between said nozzle plate and said base, said take-up assembly draws the membrane material from said spool of membrane material on said pay-out assembly through said applicator assembly.

12. A stripe applicator device comprising a frame having a first and second ends, a pay-out assembly mounted on said frame adjacent said first end of said frame, said pay-out assembly having a spool of membrane material mounted thereon, a take-up assembly mounted on said frame adjacent said second end of said frame, and an applicator assembly mounted on said frame interposed between said pay-out assembly and said take-up assembly, said applicator assembly being adapted to dispense a plurality of stripes in spaced relation along the length of the membrane material from said spool of membrane material, said applicator assembly including a plurality of nozzles having capillary orifices, said plurality of nozzles being positioned along a first line forming an obtuse angle with a second line parallel to the direction of travel of the membrane material to reduce the spacing between adjacent stripes of a plurality of stripes dispensed by said plurality of nozzles, a base mounted on said frame, a nozzle plate operably connected to said base, said plurality of nozzles being mounted in said nozzle plate, and a linear slide shaft extending from said base, and a slide slidably received over said slide shaft and connected to said nozzle plate, said slide and nozzle plate being adjustably mounted relative to said base, said take-up assembly draws the membrane material from said spool of membrane material on said pay-out assembly through said applicator assembly.

13. The stripe applicator device of claim 12, wherein said applicator assembly further comprises a micrometer mounted on said slide to adjustably maintain said slide, said nozzle plate and said plurality of nozzles mounted in said nozzle plate in spaced relation with said base.

14. A stripe applicator device comprising a frame having a first and second ends, a pay-out assembly mounted on said frame adjacent said first end of said frame, said pay-out assembly having a spool of membrane material mounted thereon, a take-up assembly mounted on said frame adjacent said second end of said frame, and an applicator assembly mounted on said frame interposed between said pay-out assembly and said take-up assembly, said applicator assembly being adapted to dispense a plurality of stripes in spaced relation along the length of the membrane material from said spool of membrane material, said applicator assembly including a plurality of nozzles having capillary orifices, said plurality of nozzles being positioned along a first line forming an obtuse angle with a second line parallel to the direction of travel of the membrane material to reduce the spacing between adjacent stripes of a plurality of stripes dispensed by said plurality of nozzles, a base mounted on said frame, a nozzle plate operably connected to said base, said plurality of nozzles being mounted in said nozzle plate, a plurality of nozzle adjustment assemblies mounted on said nozzle plate, each of said plurality of nozzle adjustment assemblies comprising a tensioning base mounted to said nozzle plate, a tensioning block having first and second ends, said tensioning block being attached at said first end to said tensioning base and extending parallel to said nozzle plate, a cantilever spring member having first and second ends, said first end of said spring being mounted interposed between said tensioning base and said first end of said tensioning block, said second end of said cantilever spring member extending beyond said second end of said tension block and attaching to one of said plurality of nozzles, and a tension adjustment screw rotatably mounted in said second end of said tensioning block and operably connected to said spring to individually adjust the spacing between one of said plurality of nozzles and said base to thereby adjust the thickness and density of one of said plurality of stripes dispensed by one of said plurality of nozzles, said take-up assembly draws the membrane material from said spool of membrane material on said pay-out assembly through said applicator assembly.

15. A stripe applicator device comprising a frame having a first and second ends, a pay-out assembly mounted on said frame adjacent said first end of said frame, said pay-out assembly having a spool of membrane material mounted thereon, a take-up assembly mounted on said frame adjacent said second end of said frame, an applicator assembly mounted on said frame interposed between said pay-out assembly and said take-up assembly, said applicator assembly being adapted to dispense a plurality of stripes in spaced relation along the length of the membrane material from said spool of membrane material, said applicator assembly including a plurality of nozzles having capillary orifices, said plurality of nozzles being positioned along a first line forming an obtuse angle with a second line parallel to the direction of travel of the membrane material to reduce the spacing between adjacent stripes of a plurality of stripes dispensed by said plurality of nozzles, a base mounted on said frame, a nozzle plate operably connected to said base, said plurality of nozzles being mounted in said nozzle plate, a plurality of vials, said plurality of vials storing a fluid having a chemical reagent emersed therein, a plurality of supply tubes, each one of said supply tubes interconnecting one of said plurality of vials with one of said plurality of nozzles, a pressure vent formed in each one of said plurality of vials, and a pressure chamber enclosing said plurality of vials, said pressure chamber being adapted to exert a pressure on the fluid in said plurality of vials through said pressure vent in each one of said plurality of vials, said take-up assembly draws the membrane material from said spool of membrane material on said pay-out assembly through said applicator assembly.

16. A stripe applicator device comprising a frame having a first and second ends.

a pay-out assembly mounted on said frame adjacent said first end of said frame, said pay-out assembly having a spool of membrane material mounted thereon, a take-up assembly mounted on said frame adjacent said second end of said frame.

an applicator assembly mounted on said frame interposed between said pay-out assembly and said take-up assembly, said applicator assembly being adapted to dispense a plurality of stripes in spaced relation along the length of the membrane material from said spool of membrane material, said applicator assembly including a plurality of nozzles having capillary orifices, said plurality of nozzles being positioned along a first line forming an obtuse angle with a second line parallel to the direction of travel of the membrane material to reduce the spacing between adjacent stripes of a plurality of stripes dispensed by said plurality of nozzles, a base mounted on said frame, a nozzle plate operably connected to said base, said plurality of nozzles being mounted in said nozzle plate, a plurality of vials, said plurality of vials storing a fluid having a chemical reagent emersed therein, a plurality of supply tubes, each one of said supply tubes interconnecting one of said plurality of vials with one of said plurality of nozzles, and a vial holder adjustably connected to said base to adjust the head pressure which supplements the capillary action of said capillary orifices in said plurality of said nozzles, said plurality of vials being retained in said vial holder said take-up assembly draws the membrane material from said spool of membrane material on said pay-out assembly through said applicator assembly.

17. The stripe applicator device of claim 16, further comprising a plurality of primer pumps, each one of said plurality of primer pumps being connected to a separate one of said plurality of vials to prime the flow of fluid from said plurality of vials out of said capillary orifices of said plurality of said nozzles.

18. A stripe applicator device comprising a frame having a first and second ends, a pay-out assembly mounted on said frame adjacent said first end of said frame, said pay-out assembly having a spool of membrane material mounted thereon, a take-up assembly mounted on said frame adjacent said second end of said frame, an applicator assembly mounted on said frame interposed between said pay-out assembly and said take-up assembly, said applicator assembly being adapted to dispense a plurality of stripes in spaced relation along the length of the membrane material from said spool of membrane material, said applicator assembly including a plurality of nozzles having capillary orifices, said plurality of nozzles being positioned along a first line forming an obtuse angle with a second line parallel to the direction of travel of the membrane material to reduce the spacing between adjacent stripes of a plurality of stripes dispensed by said plurality of nozzles, a base mounted on said frame, a nozzle plate operably connected to said base, and a plurality of nozzle assemblies mounted on said nozzle plate, each of said plurality of nozzle assemblies comprising one of said plurality of nozzles mounted in said nozzle plate, a tensioning base mounted on said nozzle plate, a tensioning block having first and second ends, said tensioning block being attached at said first end to said tensioning base and extending in space relation to said nozzle plate, a spring having first and second ends, said first end of said spring being mounted interposed between said tensioning base and said first end of said tensioning block, said second end of said spring extending beyond said second end of said tension block in a cantilever orientation, and said second end of said spring attaching to said one of said plurality of nozzles, and a tension adjustment screw rotatably mounted in said second end of said tensioning block and operably connected to said spring, said tension adjustment screw and spring being adapted to adjust the height of said one of said plurality of nozzles relative to said base.

said take-up assembly draws the membrane material from said spool of membrane material on said pay-out assembly through said applicator assembly.

19. The stripe applicator device of claim 18, further comprising a linear slide shaft extending from said base, a slide slidably received over said slide shaft and connected to said nozzle plate, and a micrometer mounted on said slide to adjustably maintain said slide, said nozzle plate and said plurality of nozzles mounted in said nozzle plate in spaced relation with said base.

20. A stripe applicator device comprising a frame having a first and second ends, a pay-out assembly mounted on said frame adjacent said first end of said frame, said pay-out assembly having a spool of membrane material mounted thereon, a take-up assembly mounted on said frame adjacent said second end of said frame, said take-up assembly including an accumulator pulley assembly, a take-up reel operably connected to said accumulator pulley assembly and a motor operably connected to said take-up reel, and an applicator assembly mounted on said frame interposed between said pay-out assembly and said take-up assembly, said applicator assembly being adapted to dispense a plurality of stripes in spaced relation along the length of the membrane material from said spool of membrane material, said applicator assembly including a plurality of nozzles having capillary orifices, said plurality of nozzles being positioned along a first line forming an obtuse angle with a second line parallel to the direction of travel of the membrane material to reduce the spacing between adjacent stripes of a plurality of stripes dispensed by said plurality of nozzles, said take-up assembly draws the membrane material from said spool of membrane material on said pay-out assembly through said applicator assembly.

21. The stripe applicator device of claim 20, wherein said take-up pulley assembly further comprises a pinch-roller operably connected to said accumulator pulley assembly.

* * * * *